United States Patent
Petersen et al.

(10) Patent No.: US 9,137,615 B2
(45) Date of Patent: Sep. 15, 2015

(54) EAR STRAP FOR A PROBE TUBE

(71) Applicant: OTICON A/S, Smørum (DK)

(72) Inventors: Svend Oscar Petersen, Smørum (DK); Bent Severin, Smørum (DK)

(73) Assignee: OTICON A/S, Smorum (DK)

( * ) Notice: Subject to any disclaimer, the term of this patent is extended or adjusted under 35 U.S.C. 154(b) by 0 days.

(21) Appl. No.: 14/290,520

(22) Filed: May 29, 2014

(65) Prior Publication Data

US 2014/0376756 A1   Dec. 25, 2014

(30) Foreign Application Priority Data

Jun. 20, 2013 (EP) ..................................... 13172994

(51) Int. Cl.
*H04R 25/00* (2006.01)
*A61B 5/12* (2006.01)
*A61B 5/00* (2006.01)

(52) U.S. Cl.
CPC ............... *H04R 25/65* (2013.01); *H04R 25/652* (2013.01); *A61B 5/121* (2013.01); *A61B 5/6816* (2013.01); *H04R 2460/17* (2013.01)

(58) Field of Classification Search
CPC .................. H04R 2225/021; H04R 2225/025; H04R 2225/063; H04R 25/02; H04R 25/60; H04R 25/65; H04R 1/105; H04R 2460/17
USPC .................................................. 381/312–331
See application file for complete search history.

(56) References Cited

U.S. PATENT DOCUMENTS

| 7,720,244 B2 | 5/2010 | Espersen et al. |
| 2002/0172386 A1 | 11/2002 | Bayer |
| 2007/0183615 A1 | 8/2007 | Wurfel |
| 2009/0092269 A1 | 4/2009 | Nielsen et al. |

FOREIGN PATENT DOCUMENTS

| DE | 83 28 154 U1 | 2/1984 |
| DE | 297 18 483 U1 | 2/1999 |
| DE | 10 2011 081 815 A1 | 12/2012 |
| EP | 1 448 014 B1 | 10/2005 |
| EP | 1 811 808 A1 | 7/2007 |
| WO | WO 2004/073349 A2 | 8/2004 |
| WO | WO 2006/026988 A1 | 3/2006 |

*Primary Examiner* — Matthew Eason
(74) *Attorney, Agent, or Firm* — Birch, Stewart, Kolasch & Birch, LLP (57) ABSTRACT

An ear strap is disclosed. The ear strap comprises attachment means configured to be attached to a tube. The ear strap has a flexible member configured to be placed within the concha of the ear and to be held in place by the concha of the ear. The flexible member is configured to take a form that fits the shape of the concha of the ear. The ear strap comprises means for adjusting the position of the tube relative to the attachment means.

19 Claims, 5 Drawing Sheets

EAR STRAP FOR A PROBE TUBE

FIELD OF INVENTION

The present invention generally relates to an ear strap for assisting arrangement of a probe tube in the ear canal. The present invention more particularly relates an ear strap that can be used to fix a probe tube in the ear canal, adjust its position in the ear canal and be attached to and be detached from the probe tube in a fast and simple way.

DESCRIPTION OF RELATED ART

A variety of hearing aids have been developed to correct the hearing of users having different degrees of hearing impairments. In many situations an individual adjusting of the hearing aid is required in order to make the hearing aid work optimal.

Such adjusting is in particular important for children and people with a high degree of hearing impairment. However, these types of adjustments are also carried out in other types of users, depending on the individual sales or delivery office tradition. The adjusting is based on a so-called "real-ear measurement", where the sound pressure inside the ear canal in front of the eardrum is measured while the patient is wearing the hearing aid.

Usually the "real-ear measurement" is carried out by the dispenser while the patient has a so-called "plug" in the ear canal. The plug is normally moulded to fit the outermost portion of the ear canal. The receiver is either provided in the plug, or placed in the hearing aid. In the latter the receiver is connected to the area in front of the eardrum by means of a tube extending through a channel in the plug.

The measurement is carried out by providing a small tube adjacent to the earplug and hereby providing an acoustic connection between the space between the plug and the eardrum and a microphone connected to the opposite end of the tube. When the receiver generates a given sound, it is possible to measure the sound pressure generated in front of the eardrum.

It is known to apply different types of strips in order to maintain e.g. an ear piece or an ear plug in the right and desired position within the ear canal.

EP 1448014 B1 discloses a behind-the-ear (BTE) hearing aid that comprises an ear piece provided with a so-called "sports lock" keeping the ear piece in place. The "sports lock" is shaped as a flexible fibre attached directly to the ear piece or via the sound tube to the ear piece. The fibre is adapted to attribute the outer ear e.g. at the lower part of the concha.

U.S. Pat. No. 7,720,244 B2 discloses an ear piece for a hearing aid that comprises a plug connected to a housing via a tube. The earpiece comprises a contact element for resting against an inside of the user's tragus and/or the ear canal and a fixture having means for adjusting the spacing between the plug and the contact element.

US 2007 183615 A1 discloses an ear canal device and a retaining strip. The ear canal device has a part configured to be inserted into the ear canal. The retaining strip is fastened to the ear canal device at its first end. The retaining strip is configured to be arranged to lie resiliently against the inside of the concha.

US 2009 092269 A1 discloses a hearing aid having a flexible elongated member with a first end attached to a shell and a second free end. The flexible elongated member has a shape for stabilizing the shell relative to a user's ear.

WO 2004 73349 A2 discloses a hearing aid system comprising a receiver configured to be inserted into the ear canal of a user. The hearing aid system comprises a connection portion extending between a sound processing component connection and the receiver. The system comprises a retaining wire configured to be positioned within a portion of the concha of the ear.

During a "real-ear measurement" it is important that the probe tube is placed and maintained at the right position. The probe tube has to be arranged so deep in the ear canal that interference from the reflected sound from the eardrum can be avoided. On the other hand the probe tube may not be placed too near to the eardrum since this can potentially damage the eardrum. When the probe tube has been placed correctly at the optimal position by the dispenser, the dispenser has to hold the probe tube fixed in this position until the ear mould or hearing aid is in place. This is a major drawback and none of the prior art systems provides a solution to this challenge.

Thus, there is a need for an improved ear strap for a probe tube, which ear strap can be used to provide and maintain a probe tube in the right position within the ear canal.

The present invention provides an ear strap that can be used to provide and maintain a probe tube in the right position within the ear canal.

Moreover, the invention also provides an ear strap that can be attached to the concha of the ear and ensure that the probe tube maintains its correct position in the ear canal.

SUMMARY OF THE INVENTION

The invention can be achieved by an ear strap as defined in claim 1. Preferred embodiments are defined in the dependent sub claims and explained in the following description and illustrated in the accompanying drawings.

The ear strap according to the invention is an ear strap comprising attachment means for being attached to a tube, where the ear strap has a flexible member configured to be placed within the concha of the ear and to be held in place by the concha of the ear, where the flexible member is configured to take a form that fits the shape of the concha of the ear. The ear strap comprises means for adjusting the position of the tube relative to the attachment means.

Here it is achieved that the ear strap can be used to provide and maintain a probe tube in the right position within the ear canal when a "real-ear measurement" has to be carried out. The ear strap can be attached to the concha of the ear and hereby it can be ensured that the probe tube maintains its correct position in the ear canal.

By the term "being attached to a tube" means that the attachment means is configured to be attached to a tube in a manner in which the attachment means and the tube are maintained fixed relative to each other.

The flexible member is configured to be placed within the concha of the ear and to be held in place by the concha of the ear. This means that the flexible member can be maintained in a position in which the flexible member is fixed to the concha of the ear. Bending of the flexible member provides a tension large enough to keep the flexible member fixed to the concha of the ear. Accordingly, the flexible member both takes a form that fits the shape of the concha of the ear and provides a mechanical attachment to the concha of the ear.

In an embodiment, the attachment means comprises an opening for receiving a tube and that the means for adjusting the position of the tube relative to the attachment means are configured to increase the size of the opening and hereby allow for attachment of the attachment means to the tube and for detachment of the attachment means from the tube.

Hereby the attachment means makes it possible to attach the attachment means to a tube and to detach the attachment means from a tube in a fast and easy manner.

In an embodiment, the means for adjusting the position of the tube relative to the attachment means is a pull out string being attached to the attachment means, where the pull out string is configured to transfer a force applied to the pull out string to the tube and hereby change the position of the tube relative to the attachment means.

Hereby it is achieved that the position of the tube relative to the attachment means can be changed and adjusted in an easy and secure way. This is useful when the ear strap is used to provide and maintain a probe tube in the right position within the ear canal when a "real-ear measurement" has to be carried out. Even when the ear strap has been attached to the concha of the ear, the position of the probe tube in the ear canal can be adjusted if desired.

In an embodiment, the pull out string is rod shaped and configured to be handled by just one or two fingers.

It may be beneficial that the attachment means is configured to be attached to a tube in such a way that the position of the tube relative to the attachment means can be changed when a force exceeding a predefined level is applied to the pull out string and that the tube is moved without changing the position of the tube relative to the attachment means when a smaller force is applied to the pull out string. In this way it is possible to use the pull out string to move the probe tube (when a small force is applied) e.g. in order to maintain the right position of the probe tube within the ear. When a larger force is applied, the position of the tube relative to the attachment means is changed (it may require that the tube is maintained in a fixed position e.g. by a hand).

In praxis the position of the tube relative to the attachment means can be changed when the applied force exceeds the retention force that is defined by the coefficient of static friction between the contact surface of the attachment means and the tube. As long as the applied force is smaller than the retention force, the attachment means will be maintained attached to the tube in the same position of attachment.

It may be beneficial that the pull out string protrudes from the attachment means and that the pull out string is rod shaped. Hereby it becomes easier to get hold of and handle the pull out string.

In an embodiment, a knob member is provided at the distal end of the pull out string. Hereby the use of the pull out string is eased. Moreover it becomes easier to get hold of and handle the pull out string.

The knob member may be spherical or have any other suitable geometrical shape.

It may be beneficial that that an aperture is provided in the attachment means.

Hereby the flexibility of the attachment means is increased so that attachment of a tube (e.g. a tube having a bend) is eased. The aperture may also make it easier to detach the tube from the attachment means.

In an embodiment, the attachment means comprises at least one pair of corresponding protruding locking members that are configured to maintain a tube attached to the attachment means once the tube has been attached to the attachment means.

Hereby a secure and reliable way of maintaining a tube attached to the attachment means can be provided. The locking members are preferably configured to allow an easy detachment of the tube from the attachment means by moving the locking members away from each other. Hereby a simple mechanical locking mechanism can be provided.

It may be beneficial that the attachment means comprises a semi cylindrical section configured to receive and bear against a tube and that the attachment means comprises a number of abutting plane sections extending basically perpendicular to the longitudinal axis of the semi cylindrical section or the attachment means.

Hereby the attachment means can be attached to a tube without damaging the tube. The tube may bear against the semi cylindrical section and at the same time be protected from damage by the structure of the semi cylindrical section. The semi cylindrical section may be provided with a surface structure or a surface layer in order to achieve any desired coefficients of friction between the tube and the contact surface of the semi cylindrical section.

In an embodiment, the opening is defined by the plane sections and the locking members. It may be beneficial that the opening has its smallest width at the region between the locking members so that the space between the locking members determines if a tube may be attached to the attachment means. It may be preferred that the locking members are configured in such a manner that the tube increases the space between the locking members the moment they pass the locking members while being inserted into the semi cylindrical section.

It may be beneficial that the attachment means comprises a body that is arranged symmetrically about the longitudinal axis of the attachment means. Hereby it is achieved that a probe tube may be attached to the attachment means regardless to the orientation of the attachment means.

It may be beneficial that the flexible member is conical so that the distal end of the flexible member has a smaller width than the proximal end of the flexible member.

Hereby the required flexibility (great flexibility of the distal end of the flexible member) and strength (great strength in the proximal end of the flexible member) of the flexible member can be provided.

In an embodiment, the longitudinal axis of the attachment means extends basically perpendicular to the longitudinal axis of the flexible member.

It may beneficial that the attachment means and the pull out string are arranged in such a way that the angle between the longitudinal axis of the attachment means and the longitudinal axis of the pull out string is smaller than 45 degrees, preferably smaller than 30 degrees.

In an embodiment, the attachment means in one end is attached at the proximal end of the flexible member and that an arm member is attached to the opposite end of the attachment means and that a pull out string is attached to the arm member. Hereby a reliable and simple ear strap can be provided.

It is preferred that the attachment means is configured to be attached to a probe tube for performing a "real-ear measurement", where the sound pressure inside the ear canal in front of the eardrum is measured while a patient is wearing a hearing aid such as a BTE hearing aid device or a receiver-in-the-ear (RITE) hearing aid device.

It may be useful to have a kit comprising an ear strap according to one of the claims and a probe tube for performing a "real-ear measurement". Such a kit may be used to carry out reliable and safe "real-ear measurement".

DESCRIPTION OF THE DRAWINGS

The invention will become more fully understood from the detailed description given herein below. The accompanying drawings are given by way of illustration only, and thus, they are not limitative of the present invention. In the accompanying drawings:

FIG. 2A) shows a first perspective view of an ear strap according to the invention, FIG. 2B) shows a second perspective view of the ear strap according to an embodiment of the invention, and FIG. 2C) shows a third perspective view of the ear strap according to an embodiment of the invention;

FIG. 3A) shows a first perspective close-up view of the attachment member of the ear strap illustrated in FIG. 2 according to an embodiment of the invention, and FIG. 3B) shows a second perspective close-up view of the attachment member of the ear strap illustrated in FIG. 2 according to an embodiment of the invention;

DETAILED DESCRIPTION OF THE INVENTION

Figure 1:
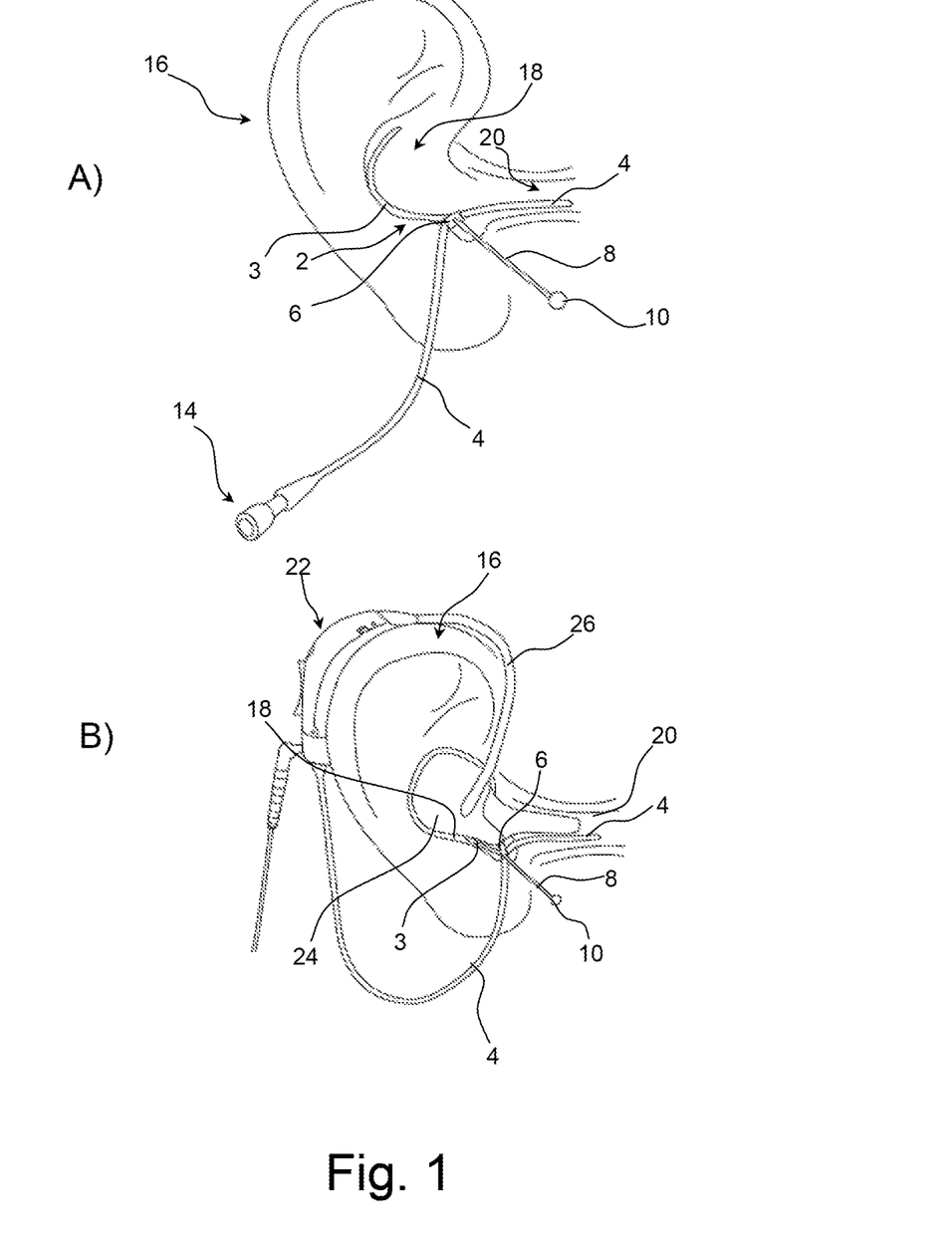
FIG. 1A) shows an ear strap attached to a probe tube that is arranged in the ear canal of a client according to an embodiment of the invention.
FIG. 1B) shows the ear strap shown in FIG. 1A) attached to maintain a probe tube extending adjacent to an earplug in a desired position in the ear canal according to an embodiment of the invention.

Referring now in detail to the drawings for the purpose of illustrating preferred embodiments of the present invention, different views of an ear strap 2 according to the invention is illustrated in FIG. 1.

FIG. 1A) illustrates an ear strap 2 according to the invention attached to a probe tube 4 that has been inserted into the ear canal 20 of a client. The ear 16 is seen from the side and the ear canal 20 is illustrated as an open canal for illustration purposes.

A microphone 14 is attached to the end of the probe tube 4. The ear strap 2 is attached to the probe tube 4 by means of an attachment member 6 (see FIG. 3-5 for a close-up view). The ear strap 2 comprises a flexible strap member 3 that is attached to the concha 18. The flexible strap member 3 (also just called a flexible member 3) is configured to take a form that fits the shape of the concha 18. The ear strap 2 moreover comprises a pull out string 8 configured to be used to adjust the position of the probe tube 4 in the ear canal 20 and to pull out the probe tube 4 from the ear canal 20. A spherical knob 10 is provided at the distal end of the pull out string 8. This knob 10 makes it easier to get hold of and use the pull out string 8.

FIG. 1B) also illustrates the ear strap 2 shown in FIG. 1A). The ear strap 2 is attached to maintain a probe tube 4 that extends adjacent to an earplug 24 (that has been inserted into the ear canal 20) in a desired position in the ear canal 20. The probe tube 4 is connected to a hearing aid device 22. The hearing aid device 22 is a BTE hearing aid device 22 that has been attached behind the ear 16 and is connected to the earplug 24 by means of a connection tube 26.

The ear strap 2 comprises a flexible strap member 3 that extends along the outside surface of the earplug 24 and is attached to the concha 18. Due to its flexibility the flexible strap member 3 has taken a form that fits the shape of the concha 18.

The ear strap 2 is provided with a pull out string 8 that is intended to be used to adjust the position of the probe tube 4 and be used to pull out the probe tube 4 from the ear canal 20. Like in FIG. 1A) a spherical knob 10 is provided at the distal end of the pull out string 8.

When the BTE hearing aid device 22 has to be adjusted a "real-ear measurement" can be carried out by detecting the sound pressure inside the ear canal 20 in front of the eardrum (not shown) while the patient is wearing the hearing aid device 22 like illustrated in FIG. 1B).

The dispenser can carry out the "real-ear measurement" while the patient has the earplug 24 inserted in the ear canal 20 like shown in FIG. 1B). The earplug 24 is moulded to fit the outermost portion of the ear canal 20.

The "real-ear measurement" is carried out by providing small probe tube 4 adjacent to the earplug 24 and hereby providing an acoustic connection between the space between the earplug 24 and the eardrum (not shown) and a microphone connected to the opposite end of the probe tube 4.

FIGS. 2A), 2B) and 2C) illustrates three perspective views of an ear strap 2 according to an embodiment of the invention. The ear strap 2 comprises an elongated strap member 3 having a distal end 38 and a proximal end 36. An attachment member 6 is provided at the proximal end 36 of the strap member 3. The attachment member 6 is configured to be attached to a probe tube (see FIG. 1A) and FIG. 1B)) in order to control the position of the probe tube.

The probe tube is intended to be attached to the attachment member 6 of the ear strap 2 by insertion of the probe tube through the opening 40. An aperture 28 is provided in the attachment member 6 for giving the required flexibility. Moreover the aperture 28 may be used when the probe tube has to be detached from the attachment member 6 of the ear strap 2.

The ear strap 2 is provided with a pull out string 8 that is intended to be used to adjust the position of a probe tube 4 and to be used to pull out the probe tube 4 from the ear canal like illustrated in FIG. 1. The pull out string 8 is attached to an arm member 12 that is attached to the attachment member 6. A spherical knob 10 is provided at the distal end of the pull out string 8.

The strap member 3 is conical and is having its greatest width at the proximal end 36 of the strap member 3 and its smallest width at the distal end 38 of the strap member 3. Hereby the required flexibility and strength of the strap member 3 can be provided.

The strap member 3 extends along its longitudinal axis X and the longitudinal axis Y of the attachment member 6 extends basically perpendicular to the longitudinal axis X of the strap member 3. The pull out string 8 is formed as a thin rod having a longitudinal axis Z. The angle $\theta$ between the longitudinal axis Y of the attachment member 6 and the longitudinal axis Z of the pull out string 8 is about 20 degrees. It is possible to provide an ear strap 2 in which the pull out string 8 is arranged differently in order to achieve a smaller angle $\theta$ between the longitudinal axis Y of the attachment member 6 and the longitudinal axis Z of the pull out string 8, e.g. an angle $\theta$ of 0, 5, 10 or 15 degrees. The angle $\theta$ between the longitudinal axis Y of the attachment member 6 and the longitudinal axis Z of the pull out string 8 may also be larger than shown in FIG. 2B), e.g. 25, 30, 35 or 40 degrees by way of example.

Figure 2:
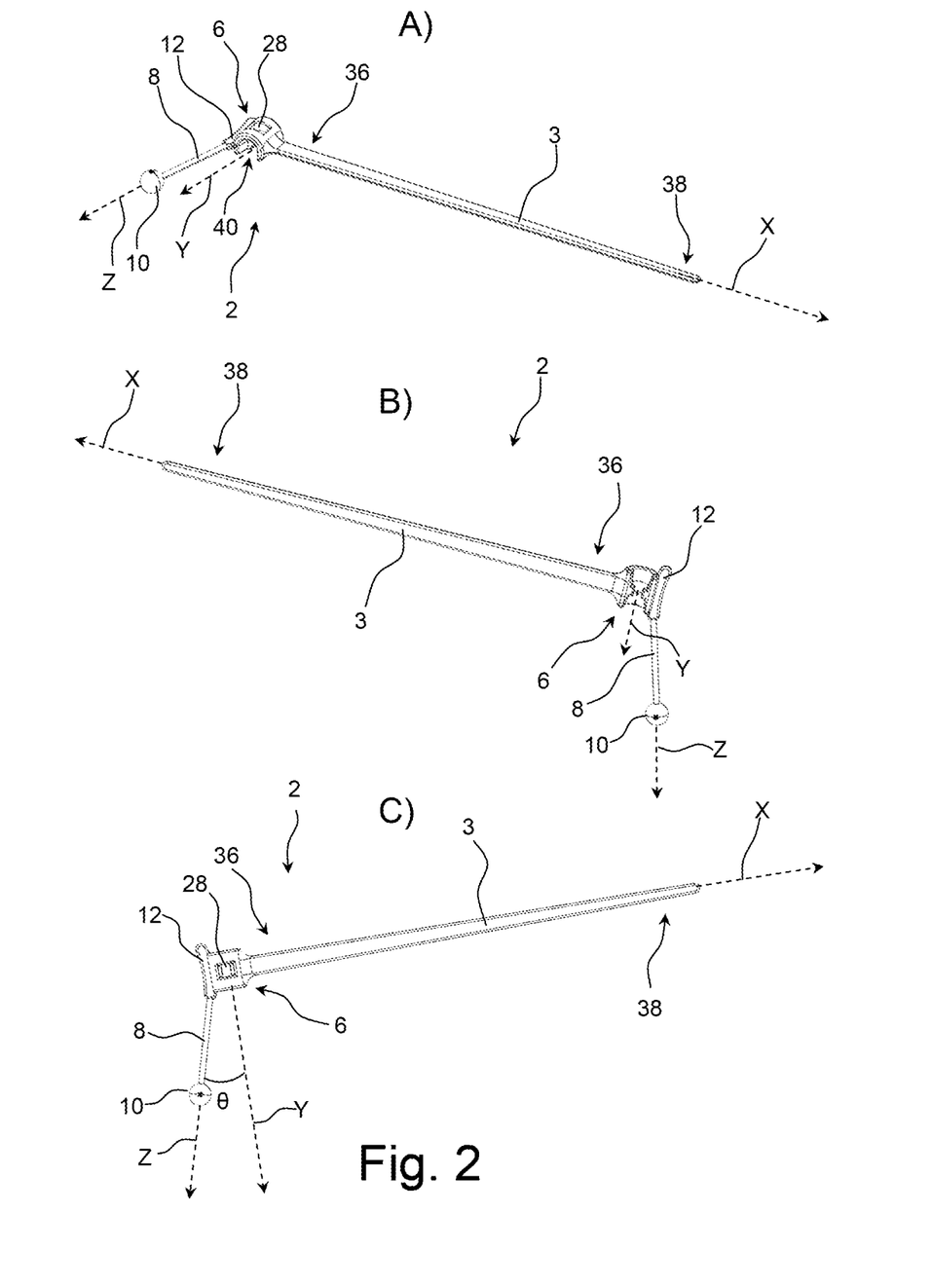
Figure 3:
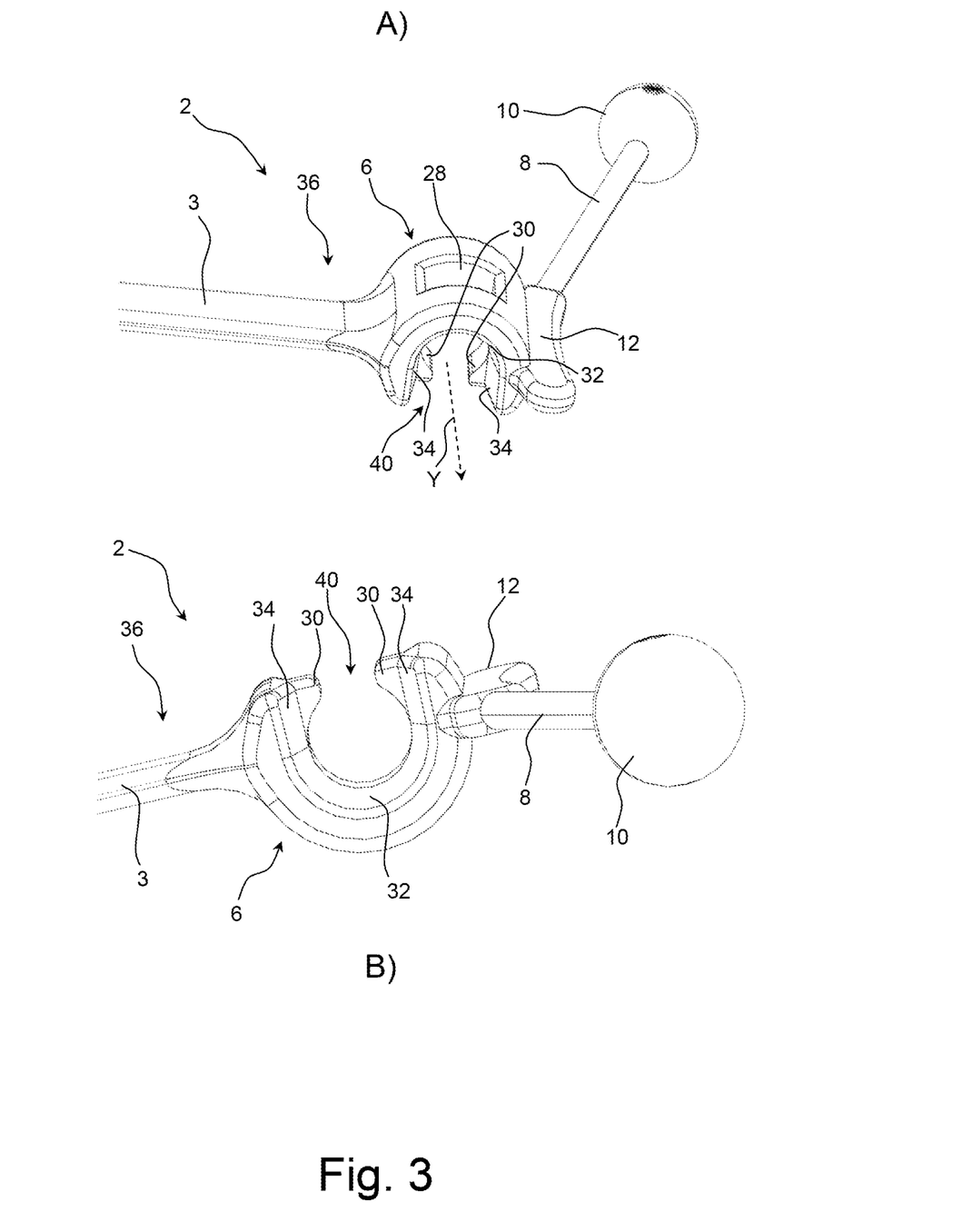

FIG. 3 illustrates two perspective close-up views of the attachment member 6 of the ear strap 2 illustrated in FIG. 1 and FIG. 2. It can be seen that the attachment member 6 is attached at the proximal end 36 of the strap member 3 of the ear strap 2.

The attachment member 6 has a body comprising a semi cylindrical section 32 and plane sections 34. An opening 40 extends along the longitudinal axis Y of the attachment member 6.

An arm member 12 is provided at the distal end of the attachment member 6 and a pull out string 8 having a spherical knob 10 attached to its free end is attached to the arm member 12.

An aperture 28 is provided in the central portion of the semi cylindrical section 32.

Two locking members 30 are provided at the midsection of the attachment member 6. The locking members 30 are basically wedge shaped and extend basically perpendicular to the longitudinal axis Y of the attachment member 6. The locking members 30 are configured to secure a probe tube (see FIG. 1) within the attachment member 6 when the probe tube has been attached to the attachment member 6.

Together with the semi cylindrical section 32 the inside surface of the locking members 30 constitutes a cylindrical portion configured to receive and bear against a probe tube. The attachment member 6 may be manufactured in a plastic, silicone or rubber material allowing the locking members 30 to be moved apart from each other in order to make it possible to insert a probe tube into the cylindrical portion through the opening 40.

Figure 4:
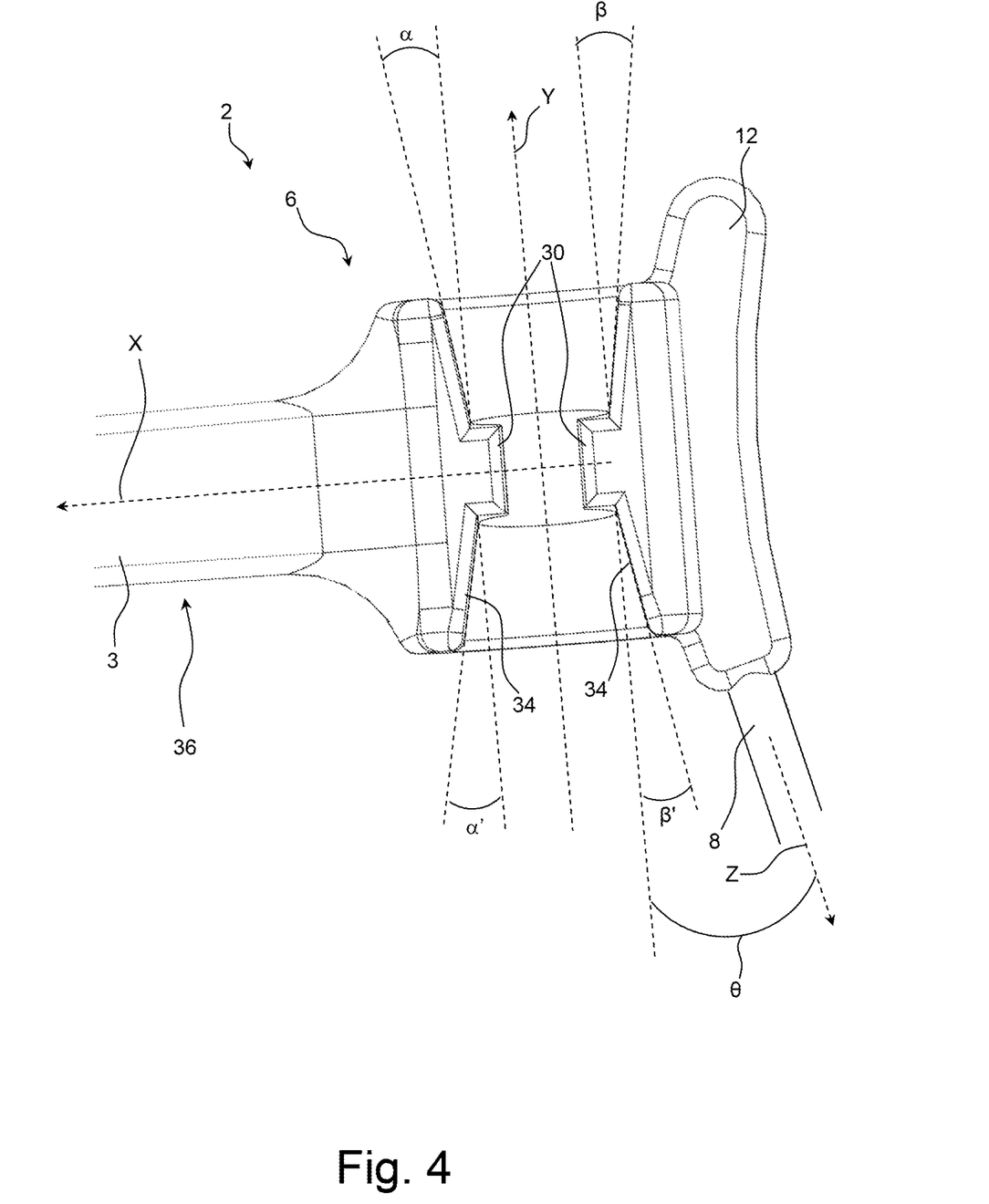
FIG. 4 shows another close-up view of the attachment member of the ear strap illustrated in FIGS. 2 and 3 according to an embodiment of the invention.

FIG. 4 illustrates another close-up view of the attachment member 6 of the ear strap 2 shown in FIG. 1-3. The attachment member 6 is symmetrical about both the longitudinal axis X of the strap member 3 and about the longitudinal axis Y of the attachment member 6. The arm member 12, however, is not completely symmetric about the longitudinal axis X of the strap member 3.

It can be seen that the angles $\alpha$, $\alpha'$, $\beta$, $\beta'$ between the plane sections 34 of the attachment member 6 and the longitudinal axis Y of the attachment member 6 is about 20 degrees. The angle $\theta$ between the longitudinal axis Y of the attachment member 6 and the longitudinal axis Z of the pull out string 8 is also approximately 20 degrees.

Figure 5:
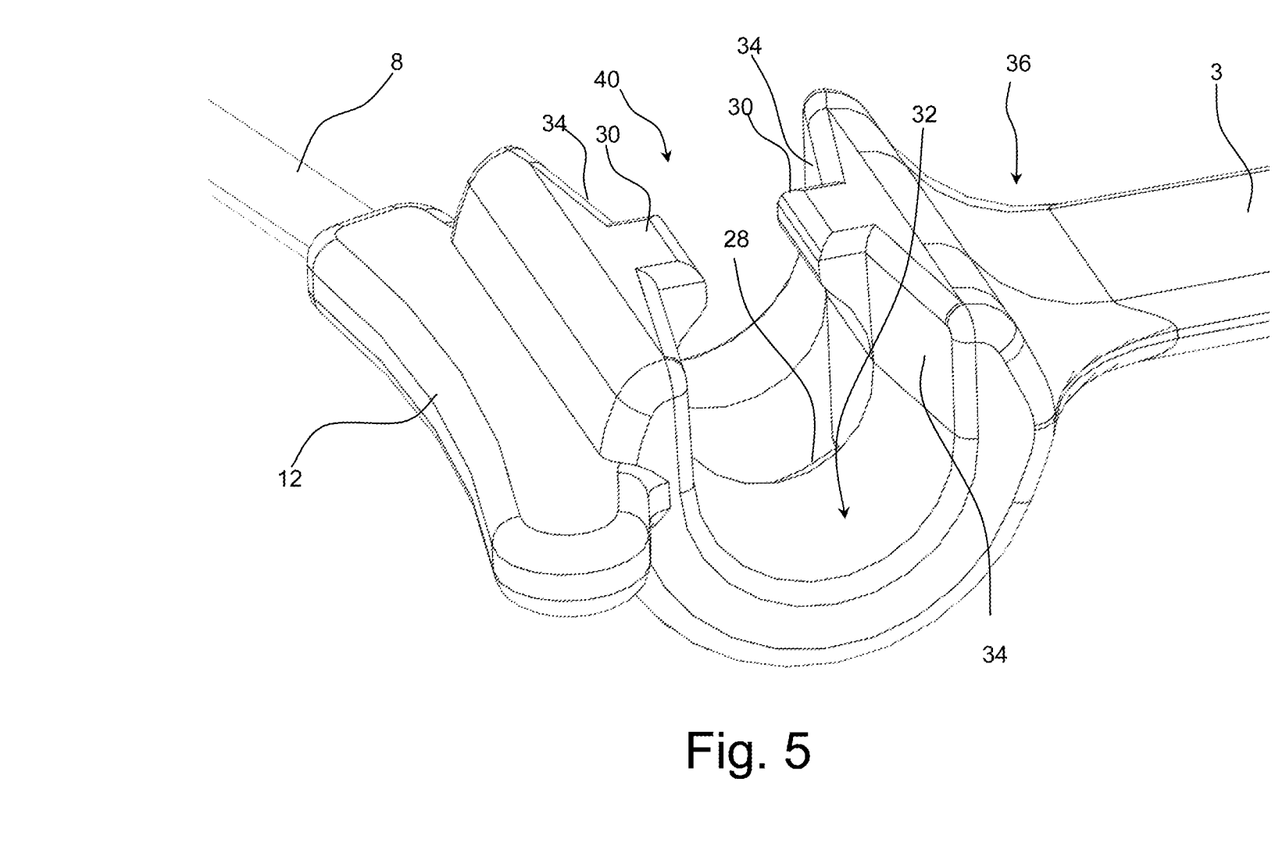
FIG. 5 shows yet another perspective close-up view of the attachment member of the ear strap illustrated in FIGS. 2-4 according to an embodiment of the invention.

FIG. 5 illustrates a close-up view of the attachment member 6 shown in FIG. 2-4. It can be seen that the locking members 30 are protruding from the plane sections 34 of the attachment member 6. Both the semi cylindrical sections 32 and the abutting plane sections 34 are smooth surfaces, however, it is possible to provide these surfaces with a structure in order to increase the friction between these surfaces and the probe tube (see FIG. 1) the attachment member 6 is configured to be attached to.

It can be seen that the pull out string 8 is integrated within the body of the attachment member 6. Hereby the pull out string 8 may be used to detach a probe tube from the attachment member 6 simply by forcing the pull out string 8 in a direction away from the strap member 3 of the ear strap 2.

It should be appreciated that reference throughout this specification to "one embodiment" or "an embodiment" or features included as "may" or "can" means that a particular feature, structure or characteristic described in connection with the embodiment is included in at least one embodiment of the invention. Therefore, it is emphasized and should be appreciated that two or more references to "an embodiment" or "one embodiment" or "an alternative embodiment" or features included as "may"/"can" in various portions of this specification are not necessarily all referring to the same embodiment. Furthermore, the particular features, structures or characteristics may be combined as suitable in one or more embodiments of the invention.

Throughout the foregoing description, for the purposes of explanation, numerous specific details were set forth in order to provide a thorough understanding of the invention.

Accordingly, the scope of the invention should be judged in terms of the claims which follow.

LIST OF REFERENCE NUMERALS

2—Ear strap
3—Strap member
4—Probe tube
6—Attachment member
8—Pull out string
10—Knob
12—Arm member
14—Microphone
16—Ear
18—Concha
20—Ear canal
22—Hearing aid device
24—Plug
26—Connection
28—Aperture
30—Locking member
32—Semi cylindrical member
34—Plane section
36—Proximal end
38—Distal end
40—Opening
X—Axis
Y—Axis
Z—Axis
$\alpha$, $\alpha'$, $\beta$, $\beta'$, $\theta$—Angle

The invention claimed is:

1. An ear strap, comprising:
an attachment part for being attached to a tube, where the ear strap has a flexible member configured to be placed within the concha of the ear and to be held in place by the concha of the ear, where a flexible member is configured to take a form that fits the shape of the concha of the ear wherein the ear strap comprises an adjuster configured to adjust the position of the tube relative to the attachment part, wherein
the attachment part comprises an opening for receiving a tube, and
the adjuster is configured to increase a size of the opening and thereby allow for attachment of the attachment part to the tube and for detachment of the attachment part from the tube.

2. An ear strap, comprising:
an attachment part for being attached to a tube, where the ear strap has a flexible member configured to be placed within the concha of the ear and to be held in place by the concha of the ear, the flexible member being configured to take a form that fits the shape of the concha of the ear, wherein the ear strap further comprises an adjuster configured to adjust the position of the tube relative to the attachment part, wherein
the adjuster is a pull out string attached to the attachment part, where the pull out string is configured to transfer a force applied to the pull out string to the tube and thereby change the position of the tube relative to the attachment part.

3. The ear strap according to claim 2, wherein the attachment part is configured to be attached to the tube in such a way that the position of the tube relative to the attachment part can be changed when a force exceeding a predefined level is applied to the pull out string and that the tube is moved without changing the position of the tube relative to the attachment part when a smaller force is applied to the pull out string.

4. The ear strap according to claim 2, wherein the pull out string protrudes from the attachment part and that the pull out string is rod shaped.

5. The ear strap according to claim 2, wherein a knob member is provided at the distal end of the pull out string.

6. An ear strap according to claim 1, wherein an aperture is provided in the attachment part.

7. An ear strap, comprising:
an attachment part for being attached to a tube, where the ear strap has a flexible member configured to be placed within the concha of the ear and to be held in place by the concha of the ear, the flexible member being configured to take a form that fits the shape of the concha of the ear, wherein the ear strap further comprises an adjuster configured to adjust the position of the tube relative to the attachment part, wherein
the attachment part comprises at least one pair of corresponding protruding locking members that are configured to maintain the tube attached to the attachment part once the tube has been attached to the attachment part.

8. The ear strap according to claim 1, wherein the attachment part comprises a semi cylindrical section configured to receive and bear against the tube and that the attachment part comprises a number of abutting plane sections extending basically perpendicular to the longitudinal axis of the semi cylindrical section or the attachment part.

9. The ear strap according to claim 1, wherein the flexible member is conical so that a distal end of the flexible member has a smaller width than a proximal end of the flexible member.

10. The ear strap according to claim 1, wherein a longitudinal axis of the attachment part extends basically perpendicular to a longitudinal axis of the flexible member.

11. The ear strap according to claim 1, wherein the attachment part and a pull out string are arranged in such a way that the angle between the longitudinal axis of the attachment part and the longitudinal axis of the pull out string is smaller than 45 degrees, preferably smaller than 30 degrees.

12. The ear strap according to claim 1, wherein the attachment part in one end is attached at a proximal end of the flexible member and that an arm member is attached to an opposite end of the attachment part and that a pull out string is attached to the arm member.

13. The ear strap according to claim 1, wherein the attachment part is configured to be attached to a probe tube for performing a "real-ear measurement", where the sound pressure inside the ear canal in front of the eardrum is measured while a patient is wearing a hearing aid such as a behind-the-ear hearing aid device or a receiver-in-the-ear hearing aid device.

14. A kit comprising an ear strap according to claim 1 and a probe tube for performing a "real-ear measurement".

15. A kit comprising an ear strap according to claim 7 and a probe tube for performing a "real-ear measurement".

16. A kit comprising an ear strap according to claim 2 and a probe tube for performing a "real-ear measurement".

17. A kit comprising an ear strap according to claim 3 and a probe tube for performing a "real-ear measurement".

18. A kit comprising an ear strap according to claim 4 and a probe tube for performing a "real-ear measurement".

19. A kit comprising an ear strap according to claim 5 and a probe tube for performing a "real-ear measurement".

* * * * *